United States Patent
Rovati et al.

(10) Patent No.: US 12,404,245 B2
(45) Date of Patent: Sep. 2, 2025

(54) PROCESS FOR THE PREPARATION OF (R)-4-(1-(6-(4-(TRIFLUOROMETHYL)BENZYL)-6-AZASPIRO[2.5]OCTANE-5-CARBOXAMIDO)-CYCLOPROPYL) BENZOIC ACID OR A SALT THEREOF

(71) Applicant: Rottapharm Biotech S.R.L., Monza (IT)

(72) Inventors: Lucio Claudio Rovati, Monza (IT); Roberto Artusi, Rho (IT); Filippo Magaraci, Monza (IT); Benedetta Buzzi, Meda (IT)

(73) Assignee: Rottapharm Biotech S.R.L., Monza (IT)

( * ) Notice: Subject to any disclaimer, the term of this patent is extended or adjusted under 35 U.S.C. 154(b) by 552 days.

(21) Appl. No.: 17/914,063

(22) PCT Filed: Mar. 19, 2021

(86) PCT No.: PCT/EP2021/057046
§ 371 (c)(1),
(2) Date: Sep. 23, 2022

(87) PCT Pub. No.: WO2021/191062
PCT Pub. Date: Sep. 30, 2021

(65) Prior Publication Data
US 2023/0127805 A1   Apr. 27, 2023

(30) Foreign Application Priority Data
Mar. 27, 2020   (EP) .................................... 20166480

(51) Int. Cl.
C07D 221/20   (2006.01)
(52) U.S. Cl.
CPC ........ C07D 221/20 (2013.01); *C07B 2200/13* (2013.01)

(58) Field of Classification Search
CPC .................. C07D 221/20; C07B 2200/13
See application file for complete search history.

(56) References Cited

U.S. PATENT DOCUMENTS

2016/0272585 A1 *   9/2016   Fisher .................. C07D 217/26

FOREIGN PATENT DOCUMENTS

| CN | 106928127 A | 7/2017 |
|---|---|---|
| WO | 2013184702 A1 | 12/2013 |

* cited by examiner

*Primary Examiner* — Timothy R Rozof
(74) *Attorney, Agent, or Firm* — Elmore Patent Law Group, P.C.; Joseph C. Zucchero; Carolyn S. Elmore (57) ABSTRACT

The present invention provides a process for preparing (R)-6-(tert-butoxycarbonyl)-6-azaspiro[2.5]octane-5-carboxylic acid (SM1), said process comprising the step of: iv) converting a compound of formula (VII) into a compound of formula (VIII) using a Wittig reagent in a suitable solvent; v) reacting through the Makosza reaction the compound of Formula (VIII) using bromoform and a suitable base to obtain cyclopropane compound of Formula (IX); and vi) removing bromine atoms in the presence of a reducing agent and a base in an alcoholic solvent thus obtaining (SM1). The invention relates also to a process for the conversion of the compound (SM1) for preparing (R)-4-(1-(6-(4-(trifluoromethyl)benzyl)-6-azaspiro[2.5]octane-5-carboxamido)cyclopropyl) benzoic acid (IV) or a salt thereof. The salt is preferably the sodium salt, more preferably the polymorphic form A of sodium (R)-4-(1-(6-(4-(trifluoromethyl)benzyl)-6-azaspiro[2.5]octane-5-carboxamido)-cyclopropyl) benzoate characterized by a powder XRD spectrum with peaks at values of the angle 2θ+0.2° of 4.3, 5.0, 5.8, 6.4, 7.1, 8.3, 8.7, 12.8, 15.3, 15.9.

15 Claims, 2 Drawing Sheets

PROCESS FOR THE PREPARATION OF (R)-4-(1-(6-(4-(TRIFLUOROMETHYL)BENZYL)-6-AZASPIRO[2.5]OCTANE-5-CARBOXAMIDO)-CYCLOPROPYL) BENZOIC ACID OR A SALT THEREOF

FIELD OF THE INVENTION

The present invention provides a process for preparing (R)-4-(1-(6-(4-(trifluoromethyl)benzyl)-6-azaspiro[2.5]octane-5-carboxamido)cyclopropyl) benzoic acid or a salt thereof, preferably the sodium salt or the polymorphic form A of sodium salt of (R)-4-(1-(6-(4-(trifluoromethyl)benzyl)-6-azaspiro[2.5]octane-5-carboxamido) cyclopropyl)benzoic acid characterized by a powder XRD spectrum with peaks at values of the angle 2θ±0.2° of 4.3, 5.0, 5.8, 6.4, 7.1, 8.3, 8.7, 12.8, 15.3, 15.9.

BACKGROUND OF THE INVENTION

The compound (R)-4-(1-(6-(4-(trifluoromethyl)benzyl)-6-azaspiro[2.5]octane-5-carboxamido)cyclopropyl) benzoic acid was firstly described in WO2013/004290 as EP4 antagonist. Specifically, the acid compound is prepared in the example 7 according to a general procedure for esters hydrolysis (method B), starting from methyl 4-(1-6-(4-(trifluoromethyl)benzyl)6-azaspiro[2,5]octane-5-carboxamido)cyclopropyl)-benzoate as single unknown enantiomer. The latter was obtained through reaction with 4-(trifluoromethyl)-benzylbromide of a racemic mixture of methyl 4-(1-(6-azaspiro[2,5]octane-5-carboxamido)cyclopropyl)benzoate, followed by chiral HPLC separation.

In the still unpublished European patent application, a method for preparing (R)-4-(1-(6-(4-(trifluoromethyl)benzyl)-6-azaspiro[2.5]octane-5-carboxamido)cyclopropyl) benzoic acid or a salt thereof is described wherein the expensive and time-consuming enantiomeric separation is avoided by using (R)-6-(tert-butoxycarbonyl)-6-azaspiro[2.5]octane-5-carboxylic acid as a starting material.

In US2016/0272585 phenoxyethyl compounds are described to be used as pharmaceuticals. In paragraphs [0102]-[0103] (R)-6-(tert-butoxycarbonyl)-6-azaspiro[2.5]octane-5-carboxylic acid is prepared through a process that provides for dissolving methyl (R)-6-tert-butoxycarbonyl-6-azaspiro[2.5]octane-5-carboxylate (in a mixture of THF and CH$_3$OH), then adding an aqueous solution of NaOH and stirring the mixture at room temperature for 1.5 h. After the addition of an aqueous solution of HCl until the pH reaches 1.0, the mixture has been extracted with EtOAc. After the layer separation, filtration and concentration under reduced pressure (R)-6-(tert-butoxycarbonyl)-6-azaspiro[2.5]octane-5-carboxylic acid was obtained. (R)-4-(1-(6-(4-(trifluoromethyl)benzyl)-6-azaspiro[2.5]octane-5-carboxamido)-cyclopropyl) benzoic acid or a salt thereof is an important pharmaceutical active ingredient to be used in a medicament or in a pharmaceutical composition.

Therefore there is still the need of preparing (R)-4-(1-(6-(4-(trifluoromethyl)benzyl)-6-azaspiro[2.5]octane-5-carboxamido)-cyclopropyl) benzoic acid or its salt in an efficient way on an industrial scale.

Therefore the object of the present invention is to produce (R)-4-(1-(6-(4-(trifluoromethyl)benzyl)-6-azaspiro[2.5]octane-5-carboxamido)-cyclopropyl) benzoic acid or its salt in an efficient way on an industrial scale.

SUMMARY OF THE INVENTION

The inventors surprisingly found out that the compound (R)-6-(tert-butoxycarbonyl)-6-azaspiro[2.5]octane-5-carboxylic acid was the key intermediate for the synthesis of (R)-4-(1-(6-(4-(trifluoromethyl)benzyl)-6-azaspiro[2.5]octane-5-carboxamido)-cyclopropyl) benzoic acid or its salts and tried to find the most efficient way to produce it.

Therefore in a first aspect the invention concerns a process for preparing (R)-6-(tert-butoxycarbonyl)-6-azaspiro[2.5]octane-5-carboxylic acid (SM 1)

said process comprising the steps of:

iv) converting a compound of formula (VII) into a compound of formula (VIII)

using a Wittig reagent in a suitable solvent;

v) reacting through the Makosza reaction the compound of Formula (VIII) using bromoform and a suitable base to obtain cyclopropane compound of Formula (IX)

and vi) removing bromine atoms in the presence of a reducing agent and a base in an alcoholic solvent thus obtaining (SM1)

In a further aspect the invention relates to a process for preparing (R)-4-(1-(6-(4-(trifluoromethyl)benzyl)-6-azaspiro[2.5]octane-5-carboxamido)cyclopropyl) benzoic acid (IV) or a salt thereof of formula:

IV said process comprising the steps of:

a) preparing (R)-6-(tert-butoxycarbonyl)-6-azaspiro[2.5]octane-5-carboxylic acid (SM1)

SM 1 through a process comprising the steps of:

iv) converting a compound of formula (VII) into a compound of formula (VIII)

using a Wittig reagent in a suitable solvent;

v) converting a compound of formula (VII) into a compound of formula (VIII)

using a Wittig reagent in a suitable solvent;

v) reacting through the Makosza reaction the compound of Formula (VIII) using bromoform and a suitable base to obtain cyclopropane compound of Formula (IX)

and vi) removing bromine atoms in the presence of a reducing agent and a base in an alcoholic solvent thus obtaining (SM1)

b) reacting the compound (R)-6-(tert-butoxycarbonyl)-6-azaspiro[2.5]octane-5-carboxylic acid (SM1) with methyl 4-(1-aminocyclopropyl)-benzoate (SM2) in the presence of a suitable coupling agent thus obtaining a compound of formula (I),

I c) N-deprotecting the compound of formula (I) in acidic media in an organic solvent to obtain a compound of formula (II)

I

II d) alkylating the nitrogen on the azaspiro[2.5]octane ring with a 4-(trifluoromethyl) benzyl bromide in presence of a suitable base to obtain compound (III)

and e) hydrolysing the methyl ester using a suitable inorganic base to obtain compound (IV)

III

IV

In a preferred and advantageous aspect, the invention relates to the process for preparing the sodium salt (Compound 1) of (R)-4-(1-(6-(4-(trifluoromethyl)benzyl)-6-azaspiro[2.5]octane-5-carboxamido)cyclopropyl) benzoic acid (IV)

Compound 1 by adding sodium hydroxide in a suitable solvent. The solvent is capable to dissolve the compound of formula (IV).

More preferably, when the solvent is propanol, then the sodium salt (Compound 1) of (R)-4-(1-(6-(4-(trifluoromethyl)benzyl)-6-azaspiro[2.5]octane-5-carboxamido)cyclopropyl) benzoic acid obtained from the compound of Formula (IV) is the polymorphic form A characterized by a powder XRD spectrum with peaks at values of the angle 2θ±0.2° of 4.3, 5.0, 5.8, 6.4, 7.1, 8.3, 8.7, 12.8, 15.3, 15.9.

The processes of the invention focused on a new way to prepare (R)-6-(tert-butoxycarbonyl)-6-azaspiro[2.5]octane-5-carboxylic acid, crucial intermediate to produce (R)-4-(1-(6-(4-(trifluoromethyl)benzyl)-6-azaspiro[2.5]octane-5-carboxamido) cyclopropyl) benzoic acid. This new way resulted to be very efficient, not only because the number of steps was reduced, but also because the complete reaction time needed to obtain the final product was almost halved as compared with the processes of prior art.

Furthermore, the purification steps resulted to be all consistent with the industrial scale, while the prior art procedure requested chromatographic columns, that are knowingly very expensive and not easily applicable on the industrial scale.

In an advantageous aspect, the process for preparing (R)-6-(tert-butoxycarbonyl)-6-azaspiro[2.5]octane-5-carboxylic acid, crucial intermediate to produce (R)-4-(1-(6-(4-(trifluoromethyl)benzyl)-6-azaspiro[2.5]octane-5-carboxamido)cyclopropyl) benzoic acid, provides only acid intermediates. They can be converted into salts in basic conditions, thus avoiding racemization. In fact, all the prior art steps involving alkyl esters needed very mild and controlled conditions to avoid racemization and consequent separation with loss of yield and time.

DETAILED DESCRIPTION OF THE INVENTION

The invention relates to a process for preparing (R)-6-(tert-butoxycarbonyl)-6-azaspiro[2.5]octane-5-carboxylicacid (SM1)

said process comprising the step of:

iv) converting a compound of formula (VII) into a compound of formula (VIII)

using a Wittig reagent in a suitable solvent;

v) reacting through the Makosza reaction the compound of Formula (VIII) using bromoform and a suitable base to obtain cyclopropane compound of Formula (IX)

and vi) removing bromine atoms in the presence of a reducing agent and a base in an alcoholic solvent thus obtaining (SM1)

Step iv) provides for a Wittig reaction. Preferably, the Witting reagent is methyl triphenyl phosphonium bromide and, independently, the solvent is selected from the group consisting of 2-methyl-tetrahydrofuran, tetrahydrofuran and toluene. The solvent is more preferably 2-methyl-tetrahydrofuran.

Step v) provides for Makosza reaction using bromoform in a suitable base, preferably the suitable base is sodium hydroxide or potassium hydroxide. The suitable base is more preferably sodium hydroxide.

In step vi) the bromine atoms are removed by using a reducing agent, preferably hydrogen and palladium on charcoal or hydrogen and Raney Nickel, more preferably hydrogen and palladium on charcoal, and a base, preferably potassium hydroxide or sodium hydroxide, more preferably potassium hydroxide, in an alcoholic solvent, preferably selected from the group consisting of isopropanol, methanol and ethanol, more preferably isopropanol, thus obtaining (R)-6-(tert-butoxycarbonyl)-6-azaspiro [2.5] octane-5-carboxylic acid (SM1).

The compound of Formula (VII) can be obtained by aspartic acid as a starting material, as indicated in Tetrahedron (1997) 15671-15680.

Specifically, the compound of Formula (VII) was obtained by following the steps of:

i) forming an ester of aspartic acid using acetyl chloride in methanol ii) reacting the compound of Formula (V) with methyl acrylate in the presence of water and a suitable base, preferably triethylamine, followed by the addition of tert-butyloxycarbonyl anhydride in tert-butanol, thus obtaining intermediate (VI);

iii) reacting the compound of Formula (VI) with sodium methoxide in tetrahydrofuran, followed by the addition of tert-butyl amine thus obtaining the compound of Formula (VII);

In a further aspect the invention relates to a process for preparing (R)-4-(1-(6-(4-(trifluoromethyl)benzyl)-6-azaspiro[2.5]octane-5-carboxamido)cyclopropyl) benzoic acid (IV) or a salt thereof of formula:

said process comprising the steps of:
a) preparing (R)-6-(tert-butoxycarbonyl)-6-azaspiro[2.5]octane-5-carboxylic acid (SM1)

through a process comprising the steps of:
iv) converting a compound of formula (VII) into a compound of formula (VIII)

using a Wittig reagent in a suitable solvent;
v) reacting through the Makosza reaction the compound of Formula (VIII) using bromoform and a suitable base to obtain cyclopropane compound of Formula (IX)

and
vi) removing bromine atoms in the presence of a reducing agent and a base in an alcoholic solvent thus obtaining (SM1)

b) reacting the compound (R)-6-(tert-butoxycarbonyl)-6-azaspiro[2.5]octane-5-carboxylic acid (SM1) with methyl 4-(1-aminocyclopropyl)-benzoate (SM2) in the presence of a suitable coupling agent thus obtaining a compound of formula (I),

SM 1

III

I c) N-deprotecting the compound of formula (I) in acidic media in an organic solvent to obtain a compound of formula (II)

and e) hydrolysing the methyl ester using a suitable inorganic base to obtain compound (IV)

I

II d) alkylating the nitrogen on the azaspiro[2.5]octane ring with a 4-(trifluoromethyl) benzyl bromide in presence of a suitable base to obtain compound (III)

II

IV

All the preferred embodiments for steps iv)-vi) as outlined before are here in step a) for preparing (R)-6-(tert-butoxy-carbonyl)-6-azaspiro[2.5]octane-5-carboxylic acid (SM1) the same.

Therefore, in step a)-iv) the Witting reagent is preferably methyl triphenyl phosphonium bromide and, independently, the solvent is 2-methyl-tetrahydrofuran, tetrahydrofuran or toluene, preferably 2-methyl-tetrahydrofuran.

In step a)-v) the suitable base is preferably sodium hydroxide or potassium hydroxide, more preferably sodium hydroxide.

In step a)-vi) the reducing agent is preferably hydrogen and palladium on charcoal or hydrogen and Raney Nickel, more preferably hydrogen and palladium on charcoal and the base is, independently, preferably potassium hydroxide or sodium hydroxide, more preferably potassium hydroxide in an alcoholic solvent selected from the group consisting of isopropanol, methanol and ethanol, preferably isopropanol.

Step b) provides for the reaction of the compound (SM1), as obtained by a process comprising the steps iv)-vi), with methyl 4-(1-aminocyclopropyl)-benzoate (SM2) in the presence of a suitable coupling agent, preferably N-(3-Dimethylaminopropyl)-N'-ethylcarbodiimide hydrochloride.

In step c) the compound (I) is N-deprotected in acidic media, preferably in trifluoroacetic acid in an organic solvent, preferably dichloromethane, to obtain compound (II).

Step d) provides for alkylating the nitrogen on the azaspiro[2.5]octane ring with 4-(trifluoromethyl)benzyl bromide in the presence of a suitable base, preferably cesium carbonate ($Cs_2CO_3$) to obtain compound (III).

In step e) the methyl ester of Formula (III) is hydrolysed by using a suitable inorganic base, preferably sodium hydroxide to obtain compound (IV).

According to the invention the compound (IV) can be converted in a pharmaceutically acceptable salt. Among these salts the following can be cited: sodium salt, potassium salt and lithium salt.

In a preferred and advantageous aspect, the invention relates to the process for preparing the sodium salt (Compound 1) of (R)-4-(1-(6-(4-(trifluoromethyl)benzyl)-6-azaspiro[2.5]octane-5-carboxamido)cyclopropyl) benzoic acid (IV)

Compound 1 by adding a sodium base, preferably sodium hydroxide, in a suitable solvent. The solvent is capable to dissolve the compound of formula (IV). Therefore, the process can provide, after step e), for a step f):

f) forming and crystallizing the sodium salt (Compound 1) in the presence of a sodium base, preferably sodium hydroxide, from the compound of Formula IV in a suitable solvent.

More preferably, when the solvent is propanol, then the sodium salt (Compound 1) of (R)-4-(1-(6-(4-(trifluoromethyl)benzyl)-6-azaspiro[2.5]octane-5-carboxamido)-cyclopropyl) benzoic acid is the polymorphic form A characterized by a powder XRD spectrum with peaks at values of the angle 2θ±0.2° of 4.3, 5.0, 5.8, 6.4, 7.1, 8.3, 8.7, 12.8, 15.3, 15.9. The powder XRD spectrum was obtained by X-ray powder diffractometer PANalytical X'pert Pro with Bragg-Brentano geometry and equipped with:

a) Detector X'Celerator, b) Multisampler, c) Spinner, d) Ceramic X-ray tube Cu LFF ($\lambda_1$=1.54051 A; $\lambda_2$=1.54430 A) Range 4-40° 2θ

As it will be clear from the experimental part the sodium salt of (R)-4-(1-(6-(4-(trifluoromethyl)benzyl)-6-azaspiro[2.5]octane-5-carboxamido)cyclopropyl)benzoic acid as obtained was an amorphous compound.

Form A is a very stable crystalline form of sodium (R)-4-(1-(6-(4-(trifluoromethyl) benzyl)-6-azaspiro[2.5]octane-5-carboxamido)cyclopropyl) benzoate. (R)-4-(1-(6-(4-(trifluoromethyl)benzyl)-6-azaspiro[2.5]octane-5-carboxamido)-cyclopropyl) benzoate, more preferably the form A is a compound capable to be used as a medicament, preferably as EP4 antagonist.

The invention will be now further detailed with reference to the experimental part.

Experimental Part

Reagents used in the following examples were commercially available from various suppliers and used without further purifications. Solvents were used in dry form. Reactions in anhydrous environment were run under a positive pressure of dry $N_2$.

Proton Nuclear Magnetic Resonance ($^1$H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH C18 column (1.7 μM, 50×2.1 mm).

The following abbreviations are used herein: AcOH: acetic acid; Boc: terbutyloxycarbonyl; DCM: dichloromethane; TFA: trifluoroacetic acid; THF: tetrahydrofuran; RT: room temperature; AcOEt: ethyl acetate; NaOH: sodium hydroxide; KOH: potassium hydroxide; TEA: triethyl amine; $Na_2SO_4$: sodium sulphate; $Cs_2CO_3$: cesium carbonate; HOBt: 1-Hydroxy benzotriazole; TBA: tert butyl amine; CTAB: cetyltrimethylammonium bromide; EDC HCl: N-(3-Dimethylaminopropyl)-N'-ethylcarbodiimide hydrochloride; IPA: isopropanol; TBME: tert butyl methyl ether.

Example 1

Preparation of Compound 1, i.e. (R)-4-(1-(6-(4-(trifluoromethyl)benzyl)-6-azaspiro [2.5]octane-5-carboxamido)cyclopropyl)benzoic acid, sodium salt Compound 1 was obtained following the synthetic steps as in the following scheme 1:

Example 1a) Synthesis of starting material 1 (R)-6-(tert-butoxycarbonyl)-6-azaspiro [2.5]octane-5-carboxylic acid (SM 1)

The starting material SM1 reported in the above scheme 1 was obtained by the following steps reported in the scheme 2 below:

Step i) Synthesis of intermediate (V) (R)-2-amino-4-methoxy-4-oxobutanoic acid hydrochloride With reference to scheme 2, the intermediate (V) was prepared.

Dry methanol (225 L) was cooled to 0-5° C., acetyl chloride (77 Kg, 1.4 eq) was added slowly. In another reactor, D-aspartic acid (90 Kg) was dissolved in dry methanol (225 L) and cooled to 0-5° C., then the pre-cooled acetyl chloride in methanol solution was added slowly maintaining the temperature at 0-5° C. The reaction was stirred at below 10° C. for 4 hours and then further for 12 hours at RT. The above reaction mass was added to TBME (800 L), cooled to 0-5° C. and stirred for 2 h. The solid obtained was filtered, washed with cold TBME (100 L) and vacuum dried for 30 minutes. Yield 92.6 kg (white solid).

$^1$H NMR (400 MHz, DMSO-$d_6$) δ ppm 13.9 (1H, bs), 8.58 (3H, bs), 4.18 (1H, m), 3.65-3.59 (3H, s), 2.98 (2H, m). ESI+m/z 148 [M+H]$^+$ Step ii) Synthesis of intermediate (VI) (R)-2-((tert-butoxycarbonyl)(3-methoxy-3-oxopropyl)amino)-4-methoxy-4-oxobutanoic acid With reference to scheme 2, the intermediate (VI) was prepared.

Water (150 L) and intermediate (V) (85 kg) were charged in a reactor, the mass was cooled to 5° C., then triethylamine (162 L, 2.5 eq) was added slowly, followed by methyl acrylate (127 L, 2.58 eq) at 0 5° C. After 4 h at RT, the reaction was washed with petrol ether (2×100 L). The aqueous layer was taken back into the reactor and diluted with tert-butanol (72 L, 1.64 eq), then Boc anhydride (127 Kg, 1.2 eq) was added slowly; the reaction was stirred for 12 hours at RT. After the reaction completion, the reaction mass was washed with petrol ether (3×70 L). The aqueous layer was taken back into the reactor, cooled to 0° C. and the pH adjusted to ~3.0 by adding concentrated HCl. The product was extracted with ethyl acetate (2×100 L) and the combined organic layers were washed with saturated citric acid solution (5×50 L). The organic layer was then washed with water (50 L), followed by brine (50 L), dried over sodium sulphate and concentrated below 55° C. Yield 114.5 kg (cream solid).

$^1$H NMR (400 MHz, CDCl$_3$) δ ppm 4.48-4.44 (1H, m), 3.75-3.67 (1H, m), 3.73 (3H, s), 3.70 (3H, s), 3.60-3.50 (1H, m), 3.16-3.10 (1H, m), 2.78-2.67 (3H, m), 1.40 (9H, s). ESI+m/z 334 [M+H]$^+$ Step iii) Synthesis of intermediate (VII) (R)-1-(tert-butoxycarbonyl)-4-oxopiperidine-2-carboxylic acid, tert-butyl amine salt With reference to scheme 2, the intermediate (VII) was prepared.

Intermediate (VI) (42 Kg) and THF (175 L) were charged in a reactor, the mass was cooled to 0-5° C., then 25% sodium methoxide solution (75 Kg, 2.84 eq) was added slowly. The reaction was refluxed for 4 h, then cooled to 25° C. and concentrated to about 45 L; water (125 L) was added, then the mixture was refluxed (~75° C.) for 14 h. The remaining THF was distilled off, then the aqueous layer was washed with ethyl acetate (3×120 L); aqueous layer was charged back into the reactor, cooled to 0° C. then the pH was adjusted to ~2.5 with concentrated HCl. The product was extracted with ethyl acetate (3×120 L), the organic layer was washed with water (150 L), followed by brine solution (150 L). The organic layer was taken back into the reactor and cooled to 0° C., and then tert-Butyl amine (10 Kg, 1.07 eq) was added to the reaction mass, stirred for 1 hour and filtered off. The product obtained was taken in IPA (120 L) and heated at 80° C. for 1 h. The mass was cooled to 10° C. and stirred for 1 h, filtered off and vacuum dried for 3 h at RT and for 8 h at 40° C. Yield 11.6 Kg (white solid).

$^1$H NMR (400 MHz, D$_2$O) δ ppm 4.56-4.39 (1H, m), 3.90-3.79 (1H, m), 3.64-3.61 (1H, m), 2.84-2.62 (2H, m), 2.53-2.43 (2H, m), 1.32 (9H, s), 1.19 (9H, s). ESI+m/z 334 [M+H]$^+$ Step iv) Synthesis of intermediate (VIII) (R)-1-(tert-butoxycarbonyl)-4-methylenepiperidine-2-carboxylic acid With reference to scheme 2, the intermediate (VIII) was prepared.

Methyltriphenylphosphonium bromide (4.38 Kg, 1.02 eq) was suspended in dry 2-MeTHF (15 L) under nitrogen; the white suspension was cooled to −8° C., then sodium tert pentoxide solution (30% in 2-MeTHF) (2.08 Kg, 2.15 eq) was dropped. After 2 hours at RT, a solution of intermediate (VII) free acid (2.92 Kg, 1.0 eq; prepared treating 3.69 Kg of intermediate (VII) tert-butylamine salt with acq. HCl and extracting with TBME) in 4 L of 2-MeTHF was added over 35 minutes. The reaction was left stirring at RT until completion (8-12 hours); then the reaction mixture was cooled to 10° C. and water (10 L) was slowly added. The layers were separated and the organic layer was washed with NaOH 0.5 N (2×5 L); the combined aqueous layers were washed with DCM (3×5 L). The aqueous layer was then acidified to pH-1 with HCl 32 wt. % (~2.5 L) and extracted with DCM (3×5 L). The combined organic layers were washed with brine (10 L), dried over Na$_2$SO$_4$ and concentrated to dryness. Obtained 2.81 Kg of intermediate (VIII) as a light brown solid (97% yield).

$^1$H NMR (400 MHz, DMSO-d$_6$) δ ppm 12.71 (1H, s), 4.78 (2H, bs), 4.75-4.60 (1H, m,), 3.92 (1H, m), 3.05-2.85 (1H, m), 2.65-2.60 (1H, m), 2.49 (1H, bs), 2.20-2.12 (2H, m), 1.42 (9H, dd, s). ESI+m/z 242 [M+H]$^+$ Step v) Synthesis of intermediate (IX) (5R)-1,1-dibromo-6-(tert-butoxycarbonyl)-6-azaspiro [2.5] octane-5-carboxylic acid With reference to scheme 2, the intermediate (IX) was prepared.

Intermediate (VIII) (3 Kg) was dissolved in DCM (25 L), CTAB (450 g; 0.1 eq.) was added, followed by warm aq. NaOH 51 wt. % (25 L). The reaction mixture was cooled to 10° C., and then bromoform (4.5 Kg, 2.13 eq) was added. After 12 h at RT, the reaction mixture was cooled to 0-5° C., water (30 L) and DCM (30 L) were added, then conc. HCl was added until pH 2. Layers were separated, aqueous phase extracted with more DCM (15 L); organic phase was washed with water (15 L), brine (15 L) and evaporated. The residue was dissolved in DCM (20 L), IPA (20 L) and water (20 L) were added; the solid precipitated was filtered, washed with water and dried. The solid was dissolved in methanol (40 L), charcoal (1.2 Kg) was added and the mixture was heated to 50° C. and filtered over a celite bed. The product was crystallized from xylene (9 L). Yield 2.72 Kg of title compound (53% yield; off-white solid).

$^1$H NMR (400 MHz, DMSO-d$_6$) δ ppm 12.94 (1H, s), 4.78 (2H, d, J=8 Hz), 3.94 (1H, m,), 3.02 (1H, m), 2.18 (1H, m), 2.15 (1H, m), 1.91-1.85 (1H, m), 1.65 (1H, d, J=2 Hz), 1.35 (11H, bs). ESI+m/z 414 [M+H]$^+$ Step vi) Synthesis of starting material 1 (SM1) (R)-6-(tert-butoxycarbonyl)-6-azaspiro[2.5]octane-5-carboxylic acid A glass autoclave was charged with intermediate (IX) (1.28 Kg), palladium on charcoal (133 g, 2.0 mol %) and a solution of KOH (1.04 Kg, 6 eq) in IPA (15 L). The autoclave was pressurized with hydrogen (5 bar) and left stirring at 65° C. for 48 hours. The black slurry reaction mixture obtained was filtered over a short celite pad that was washed with 10 L of MeOH. After removal of solvents under a reduced pressure, a white solid was obtained. It was suspended in DCM (15 L) and water (15 L), then 3 N HCl was added until pH~1 (5 L). The layers were separated and the aq. layer was extracted again with DCM (5 L). The organic layer was washed with brine (10 L), dried over Na$_2$SO$_4$ and concentrated to dryness. The solid obtained was crystallized from xylene (3 L) and dried in a vacuum oven for 5 hours to afford 0.75 Kg (92% yield) of SM1 as a white solid.

$^1$H NMR (400 MHz, chloroform-d) δ=5.11-4.77 (m, 1H), 4.18-3.88 (m, 1H), 3.32-3.09 (m, 1H), 2.32-2.14 (m, 1H), 2.03-1.88 (m, 1H), 1.67-1.55 (m, 1H), 1.50 (br s, 9H), 0.97-0.75 (m, 1H), 0.52-0.26 (m, 4H). ESI+m/z 256 [M+H]$^+$ Example 1b) Synthesis of Starting Material 2 (SM 2)

The starting material 2 (SM 2) was prepared according to known literature procedures (WO2008104055, example 1, step 2).

Example 1c) synthesis of compound (I) tert-butyl (R)-5-((1-(4-(methoxycarbonyl) phenyl)cyclopropyl) carbamoyl)-6-azaspiro[2.5]octane-6-carboxylate With reference to scheme 1, the compound (I) was obtained.

In a reactor, starting material 1 (SM1, 8 Kg) HOBt hydrate (5.8 Kg) and EDC-HCl (1.1 Kg) were dissolved in DCM (150 L) and stirred at RT; after 30 minutes, starting material 2 (SM2, 7.5 Kg) and TEA (3.4 L) were added and the reaction was left stirring for 24 hours at RT, then was quenched with water (70 L) and phases separated. The organic phase was washed with 5% sodium bicarbonate solution (2×70 L), 1 M citric acid solution (80 L), water (70 L), then DCM was evaporated. t-butylmethyl ether (17 L) was added, the suspension obtained was stirred at RT for 17 hours, then the solid was filtrated and washed with cool t-butylmethyl ether (15 L). The title compound was dried under vacuum at 50° C. for 8 hours. Yield 11.65 Kg (87%; white solid).

$^1$H NMR (400 MHz, chloroform-d) δ=8.01-7.93 (m, 2H), 7.28 (s, 2H), 6.74 (s, 1H), 4.83 (br s, 1H), 4.21 (br s, 1H), 3.92 (s, 3H), 3.10-2.87 (m, 1H), 2.10-1.99 (m, 1H), 1.97-1.85 (m, 1H), 1.84-1.75 (m, 1H), 1.52 (s, 9H), 1.40 (br s, 4H), 0.88-0.81 (m, 1H), 0.63-0.45 (m, 1H), 0.45-0.29 (m, 2H), 0.28-0.18 (m, 1H).

ESI+m/z 429 [M+H]$^+$

Example 1d): synthesis of Compound (II) methyl (R)-4-(1-(6-azaspiro[2.5]octane-5-carboxamido) cyclopropyl)benzoate With reference to scheme 1, the Compound (II) was obtained.

Compound (1) (2.56 Kg) was dissolved in DCM (22 L) at 5° C., TFA (6.7 Kg) was added and the solution stirred at RT for 5 hours. Reaction mixture was evaporated under vacuum, DCM (22 L) was added, 10% sodium bicarbonate solution was slowly added at 10-15° C. (15 L, significant foaming). Phases were separated and water discarded (pH of the aqueous phase was 7.5). Organic phase was washed with water (13 L) and evaporated at reduced pressure until 7 L of solvent were collected. t-butyl methyl ether (12 L) was added, then the solvent was evaporated again until the temperature reached 53-54° C. The suspension was cooled to 5° C. and stirred for 15-17 hours, then the solid was filtrated and washed with cool (0-5° C.) t-butylmethyl ether (5 L). The product was dried under vacuum at 60° C. for 48-72 hours. Yield 1.58 Kg (81%; white solid).

$^1$H NMR (400 MHz, chloroform-d) δ=7.96 (d, J=8.3 Hz, 2H), 7.61 (br s, 1H), 7.26 (d, J=8.3 Hz, 2H), 3.91 (s, 3H), 3.46-3.39 (m, 1H), 3.13-3.04 (m, 1H), 2.92-2.82 (m, 1H), 1.87-1.70 (m, 3H), 1.41-1.28 (m, 5H), 1.01-0.93 (m, 1H), 0.46-0.24 (m, 4H).

ESI+m/z 329 [M+H]$^+$

Example 1e) synthesis of Compound (III) methyl (R)-4-(1-(6-(4-(trifluoromethyl) benzyl)-6-azaspiro [2.5]octane-5-carboxamido)cyclopropyl)benzoate With reference to scheme 1, the intermediate (III) was obtained.

In a reactor, the compound (II) (6.6 Kg) was dissolved in dry THF (52 L), then 4-(trifluoromethyl)benzyl bromide solution in THF (5.89 Kg in 10 L of THF) and Cs$_2$CO$_3$ (12.9 Kg) were added. Reaction mixture was stirred at RT for 18 hours, and then 50 L of DCM and 30 L of water were added; aqueous phase was discarded, then organic phase was washed with water (50 L), brine (2×50 L) and evaporated at reduced pressure until 78 L of solvents were collected. Temperature was set to 40° C., then n-heptane (46 L) was added in 3 hours; solvents were distilled off until the temperature raised to 82-84° C. The mixture was cooled to 20° C. in 4 hours and stirred at this temperature for 8-10 hours; the product was filtered, washed on filter with 10 L of n-heptane and dried in a vacuum oven at 50° C. for 48 hours. Yield 5.1 Kg (91%; white solid)

1H NMR (400 MHz, chloroform-d) δ=7.96-7.89 (m, 2H), 7.66-7.61 (m, 2H), 7.47-7.40 (m, 3H), 7.27-7.21 (m, J=8.8 Hz, 2H), 3.90 (s, 3H), 3.84 (d, J=14.7 Hz, 1H), 3.35 (d, J=14.7 Hz, 1H), 3.05 (dd, J=3.9, 10.3 Hz, 1H), 2.93-2.86 (m, 1H), 2.31-2.22 (m, 1H), 2.07-1.98 (m, 1H), 1.88-1.78 (m, 1H), 1.45-1.27 (m, 4H), 1.17-1.08 (m, 1H), 1.01-0.94 (m, 1H), 0.50-0.36 (m, 3H), 0.33-0.26 (m, 1H). ESI+m/z 487 [M+H]$^+$ Example 1f): synthesis of Compound (IV) (R)-4-(1-(6-(4-(trifluoromethyl)benzyl)-6-azaspiro[2.5]oc-tane-5-carboxamido)cyclopropyl)benzoic acid With reference to scheme 1, the compound (IV), the EP4 antagonist in the form of acid (zwitterion), was obtained.

In a reactor, to a solution of compound (III) (5.1 Kg) in THF (65 L), water (39 L) and NaOH (1.67 Kg, 4 eq) were added. After stirring at 30-40° C. for 16 hours, water (25 L) was added and organics evaporated. After the addiction of 26 L of DCM, acetic acid was added until pH 4.5-5.0; the aqueous phase was discarded, the organic phase was washed with water (25 L), brine (25 L) and then evaporated. Yield 4.56 Kg (92%; white solid).

$^1$H NMR (400 MHz, DMSO-d$_6$) δ ppm 12.72 (1H, s), 8.73 (1H, s), 7.78 (2H, d, J=8.6 Hz), 7.69 (2H, d, J=8.3 Hz), 7.64 (2H, d, J=8.3 Hz), 7.20 (2H, d, J=8.6 Hz), 3.79 (2H, d, J=13.9 Hz), 3.28 (1H, d, J=13.9 Hz), 2.93 (1H, dd, J=3.1; 10.3 Hz), 2.73 (1H, m), 2.08 (2H, m), 1.78 (1H, m), 1.10-1.31 (5H, m), 0.87 (1H, m), 0.32 (4H, m). ESI+m/z 473 [M+H]$^+$.

The EP4 antagonist thus obtained was analyzed and it was found out that it was a zwitterion as an amorphous solid.

Example 1g) preparation of sodium salt of R)-4-(1-(6-(4-(trifluoromethyl)benzyl)-6-azaspiro[2.5]oc-tane-5-carboxamido)cyclopropyl)benzoic acid (Form A) (Compound 1)

In a reactor, to a solution of the compound (IV) (4.56 Kg) in n-propanol (70 L), a cooled solution of NaOH (405 g, 1.04 eq) in EtOH (9 L) was added. The suspension was stirred at RT for 20-24 hours, then filtered, washed with cool n-pro-panol (20 L) and dried at 50° C. for 24 hours under vacuum. Product was grinded (1.1 mm sieve, 3000-4000 rpm) and dried at 70° C. in vacuum for 36 hours. Yield 4.39 Kg white solid (92%) $^1$H NMR (400 MHz, DMSO-d$_6$) δ ppm 8.68 (1H, s), 7.73 (2H, d, J=8.3 Hz), 7.69 (2H, d, J=8.3 Hz), 7.64 (2H, d, J=8.3 Hz), 7.02 (2H, d, J=8.3 Hz), 3.81 (2H, d, J=13.9 Hz), 3.26 (1H, d, J=13.9 Hz), 2.92 (1H, dd, J=3.1; 10.5 Hz), 2.72 (1H, m), 2.07 (2H, m), 1.78 (1H, m), 1.16 (4H, m), 1.09 (1H, m), 0.85 (1H, m), 0.30 (4H, m).

ESI+m/z 473 [M+H]$^+$

Solubility, dissolution and bioavailability studies were performed

Characterization of sodium (R)-4-(1-(6-(4-(trifluorom-ethyl) benzyl)-6-azaspiro [2.5]octane-5-carboxamido)cyclo-propyl)benzoate (Form A) (named also as Compound 1) Solid State NMR Solid-state NMR measurements were run on a Bruker AVANCE II 400 instrument operating at 400.23 and 100.65 MHz for $^1$H and $^{13}$C, respectively. $^{13}$C CPMAS spectra were recorded at room temperature at the spinning speed of 12 kHz. Cylindrical 4 mm o.d. zirconia rotors with sample volume of 80 μL were employed. For CPMAS experiments, a ramp cross polarization pulse sequence was used with a contact time of 3 ms, a 1H 90° pulse of 4.0 μs, recycle delays of 5-10 s, and 2000-4000 transients.

The two pulse phase modulation decoupling scheme was used with a frequency field of 75 KHz $^{13}$C chemical shifts (ppm)

δ=177.1; 144.8; 143.1; 136.9; 129.3; 124.9; 71.4; 65.5; 61.3; 57.3; 51.2; 39.0; 35.1; 23.2; 18.0; 14.9; 12.6

XRPD

XRPD measurements were run on X-ray powder diffrac-tometer PANalytical X'pert Pro with Bragg-Brentano geom-etry and equipped with:
a) Detector X'Celerator
b) Multisampler
c) Spinner
d) Ceramic X-ray tube Cu LFF (λ$_1$=1.54051 A; λ$_2$=1.54430 A) Range 4-40° 2θ

| Characteristic peaks (° 2θ) |
| --- |
| 4.3 ± 0.2° 2θ |
| 5.0 ± 0.2° 2θ |
| 5.8 ± 0.2° 2θ |
| 6.4 ± 0.2° 2θ |
| 7.1 ± 0.2° 2θ |
| 8.3 ± 0.2° 2θ |
| 8.7 ± 0.2° 2θ |
| 12.8 ± 0.2° 2θ |
| 15.3 ± 0.2° 2θ |
| 15.9 ± 0.2° 2θ |

DSC

Figure 1:
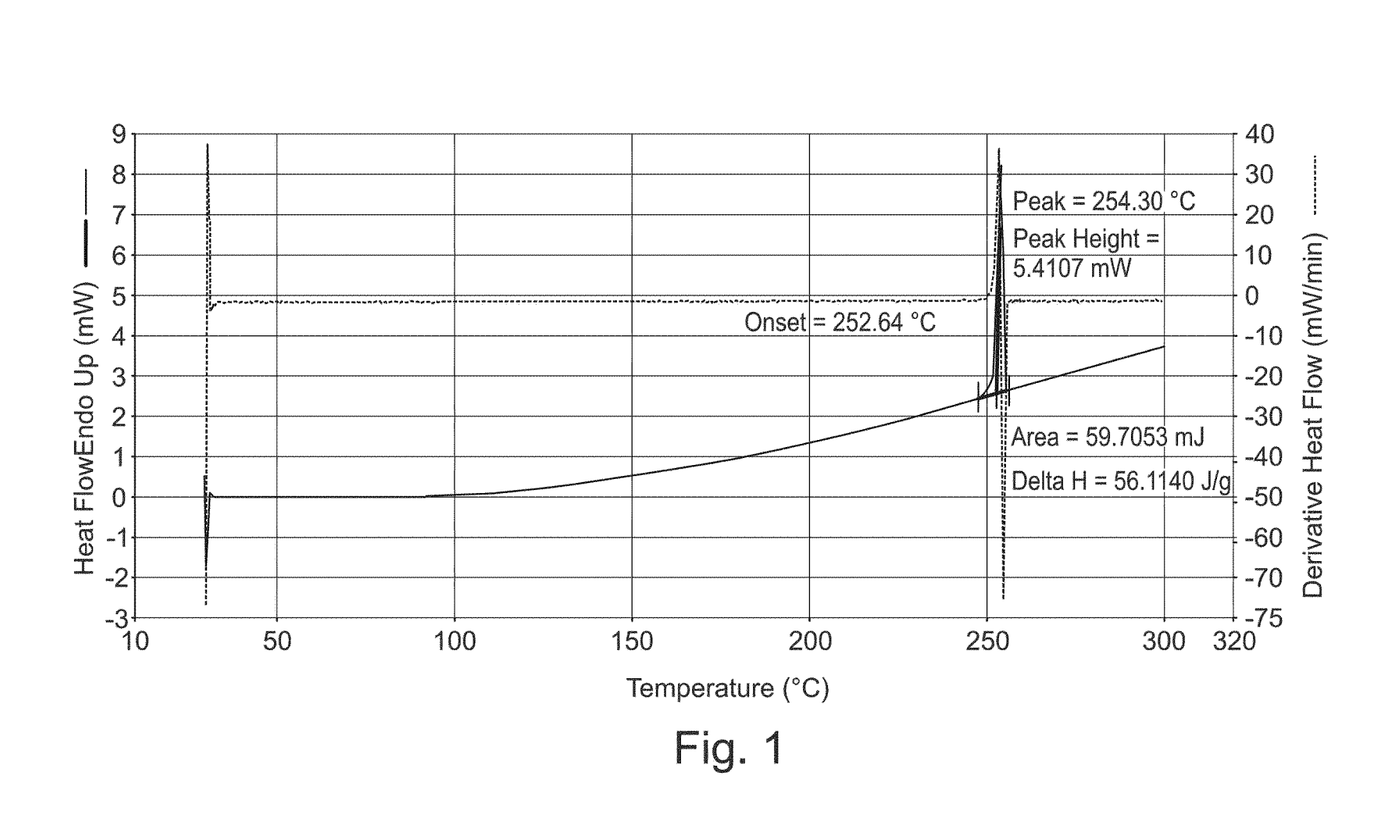
FIG. 1 reports the DSC graph of the crystalline form A of sodium (R)-4-(1-(6-(4-(trifluoromethyl)benzyl)-6-azaspiro[2.5]octane-5-carboxamido)cyclopropyl)benzoate of Example 1.

The thermogram was acquired using a Perkin-Elmer DSC8000, the scan rate was 10° C./min from 30° C. to 300° C. The thermogram is reported in FIG. 1

Detected peak: T onset=252.64° C., ΔH=56.11 J/g

IR

Figure 2:
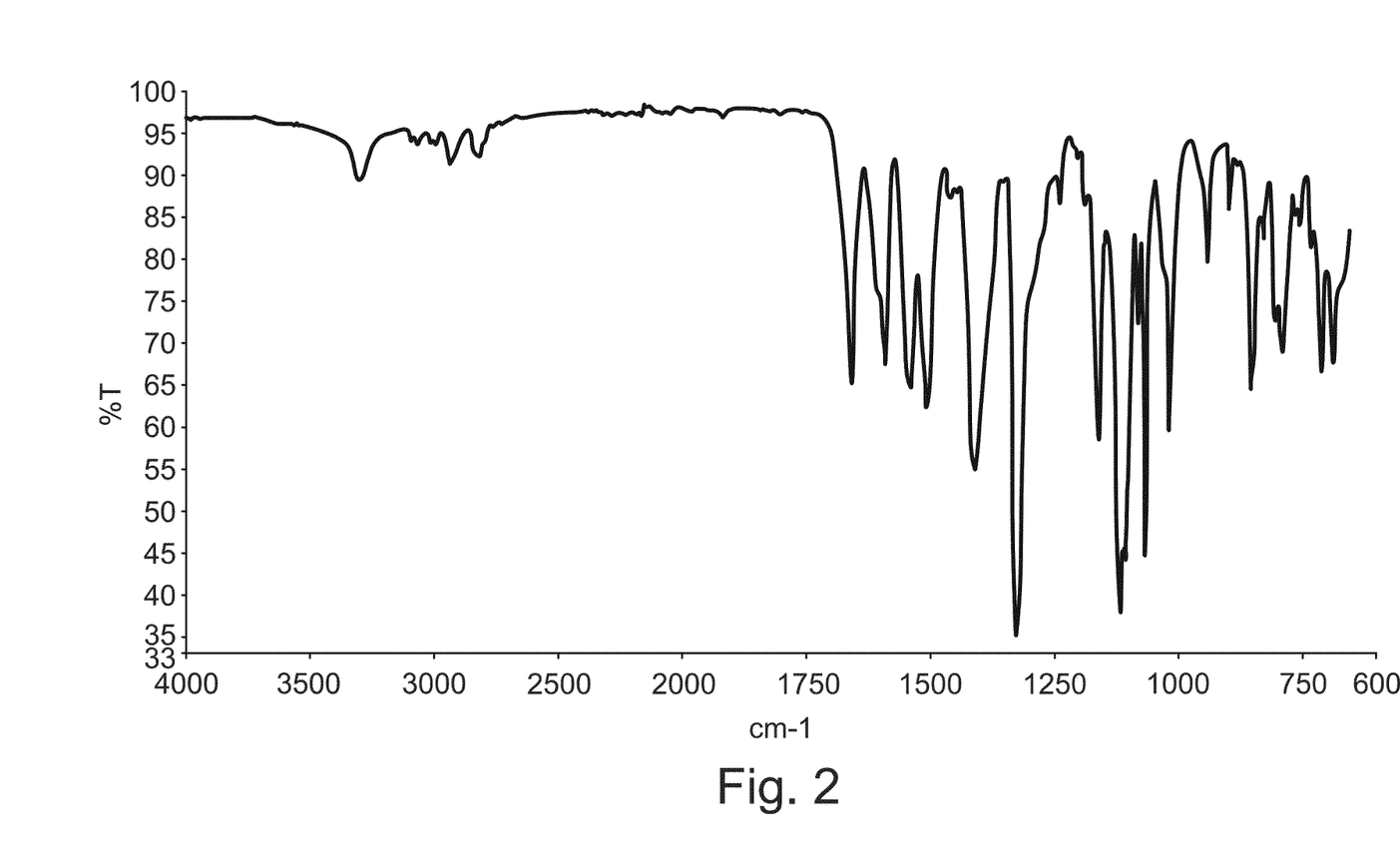
FIG. 2 reports the IR spectrum of the crystalline form A of sodium (R)-4-(1-(6-(4-(trifluoromethyl)benzyl)-6-azaspiro[2.5]octane-5-carboxamido)cyclopropyl)benzoate of Example 1.

The IR spectrum was recorded on a Perkin Elmer Spectrum 100 FT/IR instrument between 4000 and 650 cm$^{-1}$ by means of the ATR (Attenuated Total Reflectance) mode. The IR spectrum is reported in FIG. 2. The main absorption frequencies are reported in the following table:

| Band (cm$^{-1}$) |
| --- |
| 3301 |
| 2996 |
| 2938-2821 |
| 1659 |
| 1590 |
| 1540 |
| 1411 |

The invention claimed is:

1. A process for preparing (R)-6-(tert-butoxycarbonyl)-6-azaspiro[2.5]octane-5-carboxylic acid (SM1)

SM 1 said process comprising the steps of:

iv) converting a compound of formula (VII) into a compound of formula (VIII)

using a Wittig reagent in a suitable solvent;

v) reacting through the Makosza reaction the compound of Formula (VIII) using bromoform and a suitable base to obtain cyclopropane compound of Formula (IX)

and vi) removing bromine atoms in the presence of a reducing agent and a base in an alcoholic solvent thus obtaining (SM1)

2. The process according to claim 1, wherein in step iv) the Witting reagent is methyl triphenyl phosphonium bromide and, independently, the solvent is 2-methyl-tetrahydrofuran, tetrahydrofuran or toluene, preferably 2-methyl-tetrahydrofuran.

3. The process according to claim 1, wherein in step v) the suitable base is sodium hydroxide or potassium hydroxide, preferably sodium hydroxide.

4. The process according to claim 1, wherein in step vi) the reducing agent is hydrogen and palladium on charcoal or hydrogen and Raney Nickel, preferably hydrogen and palladium on charcoal and the base is, independently, potassium hydroxide or sodium hydroxide, preferably potassium hydroxide in an alcoholic solvent selected from the group consisting of isopropanol, methanol and ethanol, preferably isopropanol.

5. A process for preparing (R)-4-(1-(6-(4-(trifluoromethyl)benzyl)-6-azaspiro [2.5] octane-5-carboxamido)cyclopropyl) benzoic acid (IV) or a salt thereof of formula:

IV said process comprising the steps of:

a) preparing (R)-6-(tert-butoxycarbonyl)-6-azaspiro[2.5] octane-5-carboxylic acid (SM1)

SM 1 said process comprising the steps of:

iv) converting a compound of formula (VII) into a compound of formula (VIII)

using a Wittig reagent in a suitable solvent;

v) reacting through the Makosza reaction the compound of Formula (VIII) using bromoform and a suitable base to obtain cyclopropane compound of Formula (IX)

and vi) removing bromine atoms in the presence of a reducing agent and a base in an alcoholic solvent thus obtaining (SM1)

b) reacting the compound (R)-6-(tert-butoxycarbonyl)-6-azaspiro[2.5]octane-5-carboxylic acid (SM1) with methyl 4-(1-aminocyclopropyl)-benzoate (SM2) in the presence of a suitable coupling agent thus obtaining a compound of formula (I), c) N-deprotecting the compound of formula (I) in acidic media in an organic solvent to obtain a compound of formula (II)

d) alkylating the nitrogen on the azaspiro[2.5]octane ring with a 4-(trifluoromethyl) benzyl bromide in presence of a suitable base to obtain compound (III)

and e) hydrolysing the methyl ester using a suitable inorganic base to obtain compound (IV)

Compound 1

6. The process according to claim 5, wherein in step a)-iv) the Witting reagent is methyl triphenyl phosphonium bromide and, independently, the solvent is 2-methyl-tetrahydrofuran, tetrahydrofuran or toluene, preferably 2-methyl-tetrahydrofuran.

7. The process according to claim 5, wherein in step a)-v) the suitable base is sodium hydroxide or potassium hydroxide, preferably sodium hydroxide.

8. The process according to claim 5, wherein in step a)-vi) the reducing agent is hydrogen and palladium on charcoal or hydrogen and Raney Nickel, preferably hydrogen and palladium on charcoal and the base is, independently, potassium hydroxide or sodium hydroxide, preferably potassium hydroxide in an alcoholic solvent selected from the group consisting of isopropanol, methanol and ethanol, preferably isopropanol.

9. The process according to claim 5, wherein in step b) the coupling agent is N-(3-Dimethylaminopropyl)-N'-ethylcarbodiimide hydrochloride.

10. The process according to claim 5, wherein in step c) the compound (I) is N-deprotected in trifluoroacetic acid in an organic solvent, preferably dichloromethane.

11. The process according to claim 5, wherein in step d) the suitable base is cesium carbonate ($Cs_2CO_3$).

12. The process according to claim 5, wherein in step e) the suitable inorganic base is sodium hydroxide.

13. The process according to claim 5, wherein, after the step e), the process comprises a further step f):

f) forming and crystallizing the sodium salt (Compound 1) in the presence of a sodium base from the compound of Formula IV in a suitable solvent.

14. The process according to claim 13, wherein the sodium base is sodium hydroxide.

15. The process according to claim 13, wherein the suitable solvent is propanol, thus obtaining the sodium salt (Compound 1) of (R)-4-(1-(6-(4-(trifluoromethyl)benzyl)-6-azaspiro[2.5]octane-5-carboxamido)-cyclopropyl) benzoic acid in the polymorphic form A, characterized by a powder XRD spectrum with peaks at values of the angle 2θ±0.2° of 4.3, 5.0, 5.8, 6.4, 7.1, 8.3, 8.7, 12.8, 15.3, 15.9.

* * * * *